(12) United States Patent
Hawkes et al.

(10) Patent No.: US 8,894,687 B2
(45) Date of Patent: Nov. 25, 2014

(54) COUPLING SYSTEM FOR SURGICAL CONSTRUCT

(75) Inventors: David Hawkes, Pleasant Grove, UT (US); Ken Gardner, Smithfield, UT (US); Peter A. Halverson, Draper, UT (US)

(73) Assignee: Nexus Spine, L.L.C., Salt Lake City, UT (US)

( * ) Notice: Subject to any disclaimer, the term of this patent is extended or adjusted under 35 U.S.C. 154(b) by 0 days.

(21) Appl. No.: 13/455,854

(22) Filed: Apr. 25, 2012

(65) Prior Publication Data

US 2013/0110170 A1    May 2, 2013

Related U.S. Application Data

(60) Provisional application No. 61/478,808, filed on Apr. 25, 2011.

(51) Int. Cl.
*A61B 17/70* (2006.01)
*A61B 17/88* (2006.01)
*A61B 17/86* (2006.01)

(52) U.S. Cl.
CPC ............. *A61B 17/705* (2013.01); *A61B 17/88* (2013.01); *A61B 17/7005* (2013.01); *A61B 17/704* (2013.01); *A61B 17/8645* (2013.01); *A61B 17/7001* (2013.01)
USPC ...................................................... 606/256

(58) Field of Classification Search
USPC ......... 606/246, 250, 253, 256, 259, 260, 261, 606/262, 266, 267, 268, 269, 272, 278, 305, 606/308
See application file for complete search history.

(56) References Cited

U.S. PATENT DOCUMENTS

| 3,945,053 A | 3/1976 | Hillberry et al. |
|---|---|---|
| 5,405,408 A | 4/1995 | Pitkin |

(Continued)

FOREIGN PATENT DOCUMENTS

| EP | 1072228 | 1/2001 |
|---|---|---|
| EP | 1224915 | 7/2002 |

(Continued)

OTHER PUBLICATIONS

Jeanneau et al.; "A Compliant Rolling Contact Joint and it's Application in a 3-DOF Planar Parallel Mechanism with Kinematic Analysis"; Proceedings of DETC'04, ASME 2004 Design Engineering Technical Conferences and Computers and Information in Engineering Conference; Sep. 28-Oct. 2, 2004; Salt Lake City, Utah USA. DETC2004-57264, 2004by ASME.

(Continued)

*Primary Examiner* — Eduardo C Robert
*Assistant Examiner* — David Comstock
(74) *Attorney, Agent, or Firm* — Adam D. Stevens; Kirton McConkie (57) ABSTRACT

A coupling assembly for use in surgical constructs comprises a first body and a second body. One of the first body and the second body includes a male member and an other of the first body and the second body includes a female member. The male member is sized and shaped to be received within the female member and the female member has an internal bore sized and shaped to receive the male member therein. A raised portion is formed on or attached to the male member. An area of decreased diameter is associated with the internal bore of the female member. The first and second bodies are coupleable to one another by an interference fit when the raised portion of the male member is positioned within the area of decreased diameter associated with the internal bore of the female member.

14 Claims, 5 Drawing Sheets

(56) References Cited

U.S. PATENT DOCUMENTS

| | | |
|---|---|---|
| 5,415,661 A | 5/1995 | Holmes |
| 5,733,285 A | 3/1998 | Errico |
| 5,772,661 A | 6/1998 | Michelson |
| 5,964,760 A | 10/1999 | Richelsoph |
| 6,045,552 A | 4/2000 | Zucherman et al. |
| 6,063,089 A | 5/2000 | Errico et al. |
| 6,355,040 B1 | 3/2002 | Richelsoph |
| 6,379,354 B1 | 4/2002 | Rogozinski |
| 6,440,169 B1 | 8/2002 | Elberg et al. |
| 6,527,804 B1 | 3/2003 | Gauchet et al. |
| 6,540,785 B1 | 4/2003 | Gill et al. |
| 6,572,653 B1 | 6/2003 | Simonson |
| 6,579,320 B1 | 6/2003 | Gauchet et al. |
| 6,610,093 B1 | 8/2003 | Pisharodi |
| 6,626,904 B1 | 9/2003 | Jammet et al. |
| 6,645,248 B2 | 11/2003 | Casutt |
| 6,723,127 B2 | 4/2004 | Ralph et al. |
| 6,793,678 B2 | 9/2004 | Hawkins |
| 6,802,867 B2 | 10/2004 | Manasas et al. |
| 6,811,567 B2 | 11/2004 | Reiley |
| 6,863,688 B2 | 3/2005 | Ralph et al. |
| 6,936,071 B1 | 8/2005 | Marnay et al. |
| 6,949,123 B2 | 9/2005 | Reiley |
| 6,964,666 B2 | 11/2005 | Jackson |
| 6,966,910 B2 | 11/2005 | Ritland |
| 6,974,478 B2 | 12/2005 | Reiley et al. |
| 6,983,924 B2 | 1/2006 | Howell et al. |
| 6,991,632 B2 | 1/2006 | Ritland |
| 6,997,955 B2 | 2/2006 | Zubok et al. |
| 7,029,475 B2 | 4/2006 | Panjabi |
| 7,074,238 B2 | 7/2006 | Stinson et al. |
| 7,093,827 B2 | 8/2006 | Culpepper |
| 7,115,129 B2 | 10/2006 | Heggeness |
| 7,144,369 B2 | 12/2006 | Bardy |
| 7,207,992 B2 | 4/2007 | Ritland |
| 7,229,441 B2 | 6/2007 | Trieu et al. |
| 7,322,982 B2 | 1/2008 | Vincent-Prestigiacomo |
| 7,326,210 B2 | 2/2008 | Jahng et al. |
| 7,338,398 B2 | 3/2008 | Whiting et al. |
| 7,361,196 B2 | 4/2008 | Fallin et al. |
| 7,371,238 B2 | 5/2008 | Soboleski et al. |
| 7,377,942 B2 | 5/2008 | Berry |
| 7,445,635 B2 | 11/2008 | Fallin et al. |
| 7,458,981 B2 | 12/2008 | Fielding et al. |
| 7,476,238 B2 | 1/2009 | Panjabi |
| 7,476,251 B2 | 1/2009 | Zucherman et al. |
| 7,481,830 B2 | 1/2009 | Wall et al. |
| 7,485,133 B2 | 2/2009 | Cannon et al. |
| 7,485,134 B2 | 2/2009 | Simonson |
| 7,485,146 B1 | 2/2009 | Crook et al. |
| 7,491,218 B2 | 2/2009 | Landry et al. |
| 7,491,238 B2 | 2/2009 | Arnin et al. |
| 7,491,240 B1 | 2/2009 | Carver et al. |
| 7,494,507 B2 | 2/2009 | Dixon et al. |
| 7,537,615 B2 | 5/2009 | Lemaire |
| 7,618,441 B2 | 11/2009 | Groiso |
| 7,632,292 B2 | 12/2009 | Sengupta et al. |
| 7,682,375 B2 | 3/2010 | Ritland |
| 7,785,351 B2 | 8/2010 | Gordon et al. |
| 7,909,877 B2 | 3/2011 | Krueger et al. |
| 8,025,681 B2 | 9/2011 | Colleran et al. |
| 2002/0138077 A1 | 9/2002 | Ferree |
| 2002/0151900 A1 | 10/2002 | Glascott |
| 2003/0171751 A1 | 9/2003 | Ritland |
| 2004/0002708 A1 | 1/2004 | Ritland |
| 2004/0176849 A1 | 9/2004 | Zubok et al. |
| 2005/0038432 A1 | 2/2005 | Shaolian et al. |
| 2005/0101954 A1 | 5/2005 | Simonson |
| 2005/0113924 A1 | 5/2005 | Buttermann |
| 2005/0113927 A1 | 5/2005 | Malek |
| 2005/0125065 A1 | 6/2005 | Zucherman et al. |
| 2005/0149023 A1 | 7/2005 | Ritland |
| 2005/0159818 A1 | 7/2005 | Blain |
| 2005/0165487 A1 | 7/2005 | Muhanna |
| 2005/0177156 A1 | 8/2005 | Timm et al. |
| 2005/0192573 A1 | 9/2005 | Abdelgany et al. |
| 2005/0203516 A1 | 9/2005 | Biedermann et al. |
| 2005/0228382 A1 | 10/2005 | Richelsoph et al. |
| 2005/0240270 A1 | 10/2005 | Zubok et al. |
| 2005/0261772 A1 | 11/2005 | Filippi et al. |
| 2006/0009768 A1 | 1/2006 | Ritland |
| 2006/0009850 A1 | 1/2006 | Frigg et al. |
| 2006/0025770 A1 | 2/2006 | Schlapfer et al. |
| 2006/0036240 A1 | 2/2006 | Colleran et al. |
| 2006/0041314 A1 | 2/2006 | Millard |
| 2006/0052784 A1 | 3/2006 | Dant et al. |
| 2006/0084987 A1 | 4/2006 | Kim |
| 2006/0189983 A1 | 8/2006 | Fallin et al. |
| 2006/0190079 A1 | 8/2006 | Istephanous et al. |
| 2006/0206114 A1 | 9/2006 | Ensign et al. |
| 2006/0217712 A1 | 9/2006 | Mueller et al. |
| 2006/0229609 A1 | 10/2006 | Wang |
| 2006/0240533 A1 | 10/2006 | Sengupta et al. |
| 2006/0271047 A1 | 11/2006 | Jackson |
| 2006/0271051 A1 | 11/2006 | Berrevoets |
| 2007/0016193 A1 | 1/2007 | Ritland |
| 2007/0028714 A1 | 2/2007 | Lusk et al. |
| 2007/0043365 A1 | 2/2007 | Ritland |
| 2007/0049936 A1 | 3/2007 | Colleran et al. |
| 2007/0088440 A1 | 4/2007 | Eisermann et al. |
| 2007/0179618 A1 | 8/2007 | Trieu et al. |
| 2008/0015588 A1 | 1/2008 | Hawkes |
| 2008/0077246 A1 | 3/2008 | Fehling et al. |
| 2008/0140075 A1 | 6/2008 | Ensign |
| 2008/0154308 A1 | 6/2008 | Sherman et al. |
| 2008/0167688 A1 | 7/2008 | Fauth et al. |
| 2008/0183209 A1 | 7/2008 | Robinson et al. |
| 2008/0195208 A1 | 8/2008 | Castellvi |
| 2008/0195213 A1 | 8/2008 | Halverson et al. |
| 2008/0234739 A1 | 9/2008 | Hudgins et al. |
| 2008/0312693 A1 | 12/2008 | Trautwein et al. |
| 2009/0005819 A1 | 1/2009 | Ben-Mokhtar et al. |
| 2009/0048631 A1 | 2/2009 | Bhatnagar et al. |
| 2009/0228045 A1 | 9/2009 | Hayes et al. |
| 2009/0259257 A1 | 10/2009 | Prevost |
| 2009/0270921 A1 | 10/2009 | Krause |
| 2010/0204732 A1 | 8/2010 | Aschmann et al. |
| 2010/0211106 A1 | 8/2010 | Bowden et al. |
| 2010/0217324 A1 | 8/2010 | Bowden et al. |
| 2010/0217326 A1 | 8/2010 | Bowden et al. |
| 2010/0217334 A1 | 8/2010 | Hawkes |
| 2010/0222821 A1 | 9/2010 | Bowden et al. |
| 2010/0222823 A1 | 9/2010 | Bowden et al. |
| 2010/0241232 A1 | 9/2010 | Halverson et al. |

FOREIGN PATENT DOCUMENTS

| | | |
|---|---|---|
| EP | 1970031 | 9/2008 |
| KR | 1020050080493 | 8/2005 |
| KR | 1020060113318 | 11/2006 |
| WO | WO 2004/071344 | 8/2004 |
| WO | WO 2005/051243 | 6/2005 |
| WO | WO 2005/107654 | 11/2005 |
| WO | WO 2006/127992 | 11/2006 |
| WO | WO 2007/041265 | 4/2007 |
| WO | WO 2008/070840 | 6/2008 |
| WO | WO 2008/100891 | 8/2008 |
| WO | WO 2010/030906 | 3/2010 |
| WO | WO 2010/096621 | 8/2010 |
| WO | WO 2010/096829 | 8/2010 |
| WO | WO 2010/108010 | 9/2010 |

OTHER PUBLICATIONS

Cannon et al.; "Compliant Rolling-Contact Element Mechanisms"; Proceedings of IDETC/CIE 2005, 2005 ASME Design Engineering Technical Conferences & Computers and Information in Engineering Conference, Sep. 24-28, 2005, 2005; Long Beach, California, USA; DETC2005-84073.

Halverson et al.; "Concepts for Achieving Multi-Stability in Compliant Rolling-Contact Elements"; Proceedings of IDETC/CIE 2007; ASME 2007 International Design Engineering Technical Conferences & Computers and Information in Engineering Conference;

(56) References Cited

OTHER PUBLICATIONS

Sep. 24-28, 2007; Las Vegas, USA; DETC2007-34836.

Halverson et al.; Tension-Based Multi-Stable Compliant Rolling-Contact Elements'; 13th National Conference on Mechanisms and Machines (NaCoMM-2007); IISc, Bangalore, India; Dec. 12-13, 2007.

Jacobsen et al.; "Components for the Design of Lamina Emergent Mechanism"; Proceedings of IMECE 2007, 2007 ASME International Mechanical Engineering Congress and Exposition; Nov. 10-16, 2007; Seattle, USA.

Jacobsen et al.; "Mechanism and Machine Theory"; Mechanism and Machine Theory; 2009; pp. 2098-2109; vol. 44; Elsevier.

Stratton et al.; Force-Displacement Model of the Flexsure™ Spinal Implant; Proceedings of the ASME 2010 International Design Engineering Technical Conferences and Computers and Information in Engineering Conference IDETC/CIE; Aug. 15-18, 2010; Montreal, Quebec, Canada.

U.S. Appl. No. 12/916,110, filed Oct. 29, 2010; Spencer P. Magleby.

U.S. Appl. No. 12/711,131, filed Feb. 23, 2010; David R. Hawkes; office action dated Jun. 4, 2012.

U.S. Appl. No. 12/711,131, filed Feb. 23, 2010; David T. Hawkes; office action dated Dec. 26, 2012.

U.S. Appl. No. 11/952,709, filed Dec. 7, 2007; Michael D. Ensign; office action dated Nov. 6, 2013.

U.S. Appl. No. 11/284,438, filed Nov. 21, 2005; Michael D. Ensign; office action dated Nov. 12, 2013.

International application No. PCT/US2013/066292; filing date Oct. 23, 2013; Nexus Spine, L.L.C.; International Search Report mailed Jan. 22, 2014.

U.S. Appl. No. 12/711,131, filed Feb. 23, 2010; David T. Hawkes; office action dated Mar. 24, 2014.

U.S. Appl. No. 12/709,240, filed Feb. 19, 2010; Anton E. Bowden; office action dated Apr. 22, 2013.

U.S. Appl. 12/726,816, filed Mar. 18, 2010; Peter Halverson; office action issued Jan. 31, 2013.

PCT Application PCT/US2012/041360; filing date Jun. 7, 2012; Eric Dodgen; International Search Report mailed Dec. 14, 2012.

U.S. Appl. 12/916,110, filed Oct. 29, 2010; Spencer P. Magleby; office action issued Dec. 14, 2012.

COUPLING SYSTEM FOR SURGICAL CONSTRUCT

PRIORITY CLAIM

Priority is claimed of U.S. Provisional Patent Application Ser. No. 61/478,808, filed Apr. 25, 2011, which is hereby incorporated herein by reference in its entirety.

RELATED CASES

This application is related to U.S. patent application Ser. No. 12/711,131, filed Feb. 23, 2010, which is hereby incorporated herein by reference in its entirety.

BACKGROUND OF THE INVENTION

1. Field of the Invention

The present invention relates generally to the field of coupling systems for use in surgical implants. More particularly, the present invention relates to such systems for use in orthopedic rod fixation systems.

2. Related Art

Bone stabilization/fixation devices to align or position bones have been used for some time. Such devices have been used to align or position specific vertebrae, or a specific region of the spine. Typically, such devices utilize a coupling assembly to connect or link two or more surgical screws and/or pedicle screws together to stabilize the bone and/or joint around which the screws are fixed. Conventional coupling assemblies are typically comprised of a relatively rigid member, such as a plate or a rod, that is used to couple or join adjacent structures or parts of the anatomy. Once the coupled structures are spatially fixed in position, surgical procedures can be completed and healing can proceed.

The present inventor has found, however, that such conventional surgical and/or pedicle screw coupling systems have several drawbacks. For example, such systems are rather large and bulky, which can result in increased tissue damage in and around the surgical site, resulting both from installation of the coupling system during surgery and from implant induced, post-operative tissue irritation and erosion. The relative bulk of prior art devices can be particularly troublesome in supra-fascial applications.

Some prior art coupling systems have a rod-receiving device that is delivered to the surgeon already coupled or attached to the head of the surgical screw, which poses two challenges: 1) this prevents certain surgical maneuvers (e.g. placing the screws prior to interbody work); and, 2) increases the carrying cost of the inventory. Furthermore, traditional coupling systems do not allow for varying the rod stiffness along a multi-segmented construct; certain indications may require a stiff rod over one segment and a flexible rod over another.

Further, traditional systems inherently possess an inability to easily extend a fusion: e.g., in a revision procedure, the existing rod would need to be either completely removed and replaced with a new rod or cut in vivo. In addition, some of the prior art coupling systems include locking components (e.g., set screws and the like) that must all be carefully assembled together during the surgical procedure. Further, many traditional surgical screw system designs complicate or even preclude the ability to be placed percutaneously over a guide wire, which makes these systems more difficult to install and maneuver during surgical procedures, including minimally invasive procedures.

Furthermore, many prior art devices require that the rod be attached to the coupling device after the screw is inserted in the bone, which can be disadvantageous at times, whereas the option to assemble the rod to the coupling device outside the wound may prove valuable. Also, existing coupling systems often necessitate simultaneous locking of all components, which prevents the ability to properly compress a coupling system along the rod because the angle relative to the surgical screw would change.

Furthermore, predicate technology necessitates bending of the rod for multi-segmented constructs. Rod bending is not only cumbersome to perform, but invariably results in an unintended stress applied to the bones.

SUMMARY OF THE INVENTION

In accordance with one aspect of the invention, a coupling assembly for use in surgical constructs is provided, including a first body and a second body. One of the first body and the second body includes a male member and an other of the first body and the second body includes a female member. The male member is sized and shaped to be received within the female member and the female member has an internal bore sized and shaped to receive the male member therein. A raised portion can be formed on or attached to the male member. An area of decreased diameter can be associated with the internal bore of the female member. The first and second bodies are coupleable to one another by an interference fit when a portion of the male member is positioned within an area of smaller diameter associated with the internal bore of the female member.

In accordance with another aspect of the invention, a coupling assembly for use in surgical constructs is provided, including a first body and a second body. One of the first body and the second body can include a male member and an other of the first body and the second body can include a female member. The male member is sized and shaped to be received within the female member and the female member can have an internal bore sized and shaped to receive the male member therein. A raised portion can be formed on or attached to the male member. A cinch band can be applied to an outer portion of the female member that applies a compressive force to the female member to create an area of decreased diameter within the internal bore of the female member. The first and second bodies can be coupleable to one another by an interference fit when the raised portion of the male member is positioned within the area of decreased diameter in the internal bore of the female member.

In accordance with another aspect of the invention, a method of coupling portions of a surgical construct to one another is provided, including: obtaining a first body and a second body, one of the first body and the second body including a male member and an other of the first body and the second body including a female member, the male member being sized and shaped to be received within the female member and the female member having an internal bore sized and shaped to receive the male member therein; positioning a raised portion formed on or attached to the male member within the internal bore of the female member; and creating an area of decreased diameter within the internal bore of the female member about or around the raised portion of the male member to thereby couple the first body and the second body to one another by an interference fit.

In accordance with another aspect of the invention, a method of implanting a coupling assembly within a patient is provided, including: attaching one of a first body and a second body to a first surgical screw, one of the first body and the second body including a male member and an other of the first body and the second body including a female member, the male member being sized and shaped to be received within the female member and the female member having an internal bore sized and shaped to receive the male member therein; positioning a raised portion formed on or attached to the male member within the internal bore of the female member; and creating an area of decreased diameter within the internal bore of the female member about or around the raised portion of the male member to thereby couple the first body and the second body to one another by an interference fit.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The following drawings illustrate exemplary embodiments for carrying out the invention. Like reference numerals refer to like parts in different views or embodiments of the present invention in the drawings.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Definitions

As used herein, the singular forms "a" and "the" can include plural referents unless the context clearly dictates otherwise. Thus, for example, reference to "a coupler" can include one or more of such couplers.

As used herein, the term "substantially" refers to the complete or nearly complete extent or degree of an action, characteristic, property, state, structure, item, or result. As an arbitrary example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item as long as there is no measurable effect thereof.

As used herein, the terms "attached," "coupled," "fixed," etc., can be used to describe a condition in which two or more components are coupled to one another in such a manner that they function as intended: that is, the force required to uncouple the components is sufficiently large such that the components will remain attached to one another during the service for which they were designed. Unless indicated to the contrary, such "coupled" components can be separable if sufficient force is applied to the components. In some aspects of the invention, components are elastically fixed or coupled to one another and will remain fixed during the useful life of the product for which they are designed; however, they may be uncoupled from one another using an appropriate level of force (applied in an appropriate manner and location), and will return to an original configuration (e.g., a condition, state, shape, size, etc.), which existed prior to the components being coupled to one another.

As used herein, when an area within a construct body is described as having a "decreased diameter," it is to be understood that the area described includes a diameter that is smaller than adjacent areas (either on one or both sides of the area of decreased diameter). For example, an area within a bore may have a decreased diameter as compared to other portions of the bore. In some embodiments, the area of decreased diameter within the bore will appear (although possibly not to the human eye) as an inner "rib," or raised portion, having a smaller diameter than adjacent portions.

Figure 1:
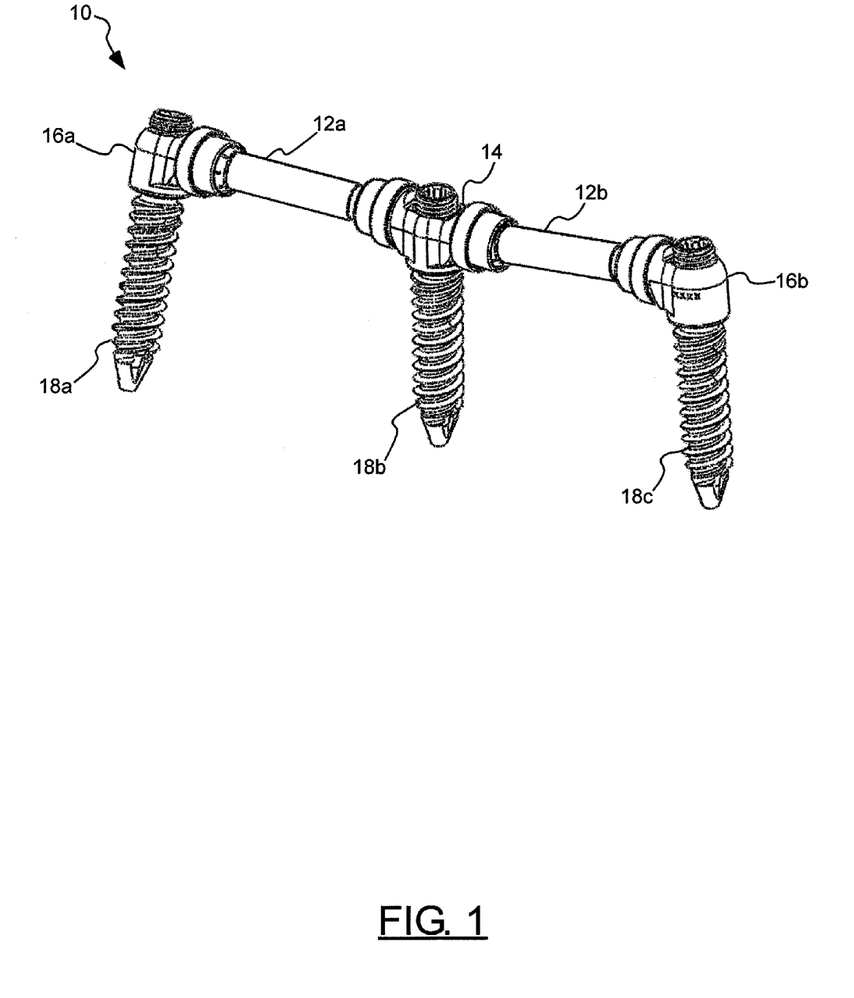
FIG. 1 is a perspective view of an embodiment of the invention including several bodies interconnected to one another and attached to surgical screws (note that the attachment systems shown have not yet been fixed in place relative to one another in this view)

The term "body" can be used herein to refer to a variety of components of a surgical construct. For example, several components are illustrated in FIG. 1, including connecting rods 12a, 12b, "T" coupler 14, end couplers 16a, 16b, etc. Each of these components can be included within the scope of the meaning of the term "body." Typically speaking, surgical screws 18a, 18b, 18c are not referred to herein as "bodies;" however, a specific discussion of one or more embodiments may dictate otherwise, as would be appreciated by one of ordinary skill in the art having possession of this disclosure.

As used herein, the term "interference fit" shall be interpreted broadly as including the joining of any two mating parts such that one or the other (or both) parts slightly deviate in size from their nominal dimension, thereby deforming such part slightly, each being compressed, the interface between two parts creating a union of extremely high friction. The word "interference" refers to the fact that one part slightly interferes with the space that the other is occupying in its nominal dimension. In one aspect of the invention, interference fit can be configured to require at least about 800 pounds of force to remove a male member from a female member. In one aspect of the invention, interference fit can be configured to require at least about 400 pounds of force to remove a male member from a female member. In one aspect of the invention, interference fit can be configured to require at least about 1200 pounds of force to remove a male member from a female member.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present invention relates generally to surgical construct systems that can include a variety of coupling assemblies that are used to connect a variety of surgical screws. The surgical screws generally include a threaded portion which is used to implant the screws into the body of a patient, often into bone of the patient. The present system is suitable for use with a variety of orthopedic rod placement devices, hooks, and/or surgical screws, including, but not limited to, pedicle screws and orthopedic rods used in spinal surgery.

Figure 2:
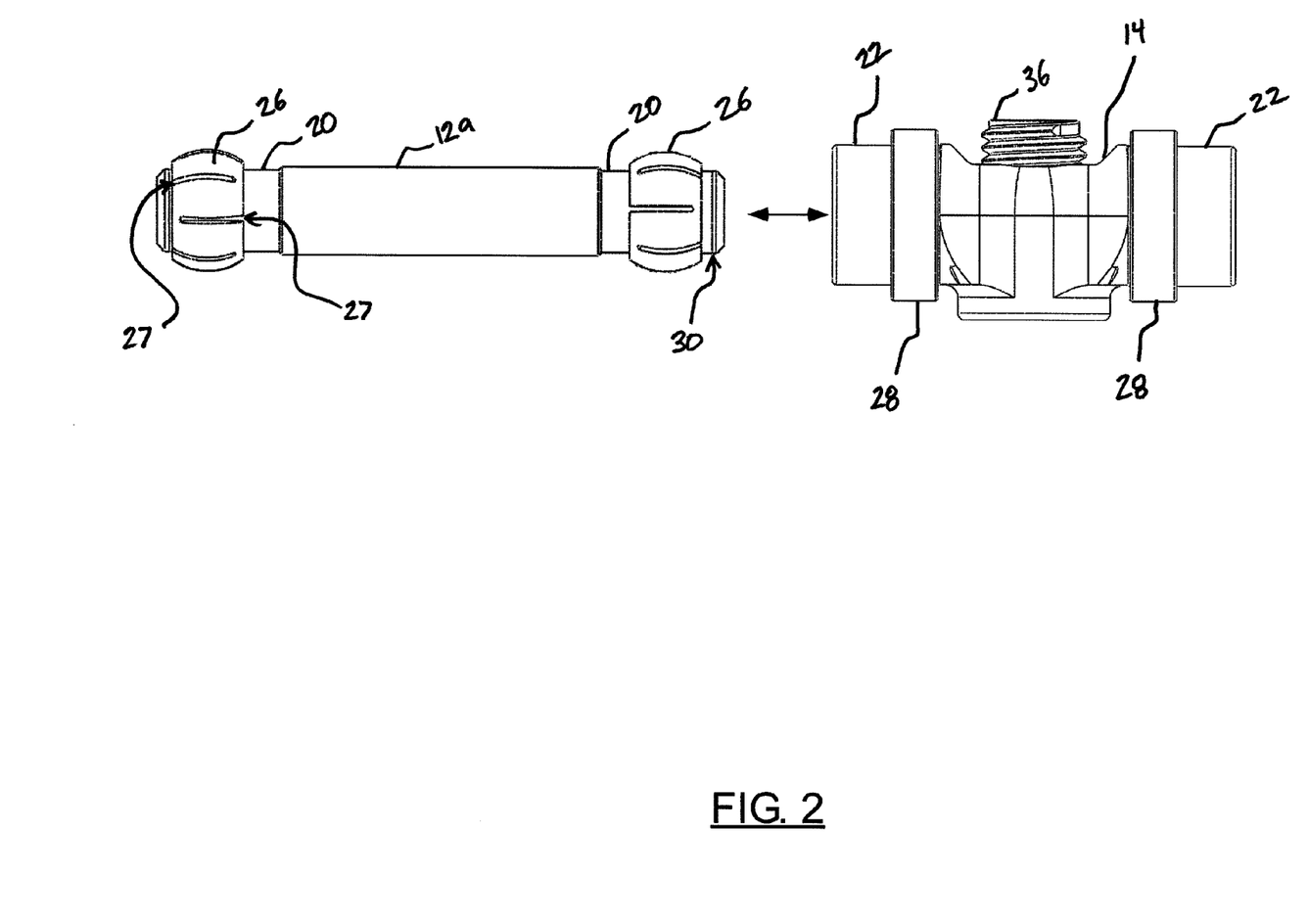
FIG. 2 illustrates a linking rod assembly and a coupler in accordance with an embodiment of the invention.

As shown specifically in FIGS. 1 and 2, in one exemplary embodiment of the invention, a coupling assembly 10 is provided. In this aspect of the invention, the assembly includes three surgical screws 18a, 18b and 18c. The screws can be interconnected to one another by way of end couplers 16a, 16b, "T" coupler 14 and rod connectors 12a, 12b. The assembly can be used in a variety of surgical applications, including, but not limited to, spinal implant surgeries. Among a variety of other improvements, the present invention provides robust and durable coupling assemblies that have a smaller profile with fewer components and greater ease of assembly with more surgical options than prior art devices. It is believed that the embodiments, collectively and/or individually, represent an unexpected advance in the field and will enable physicians to more easily adjust and/or accommodate for various factors.

Figure 3:
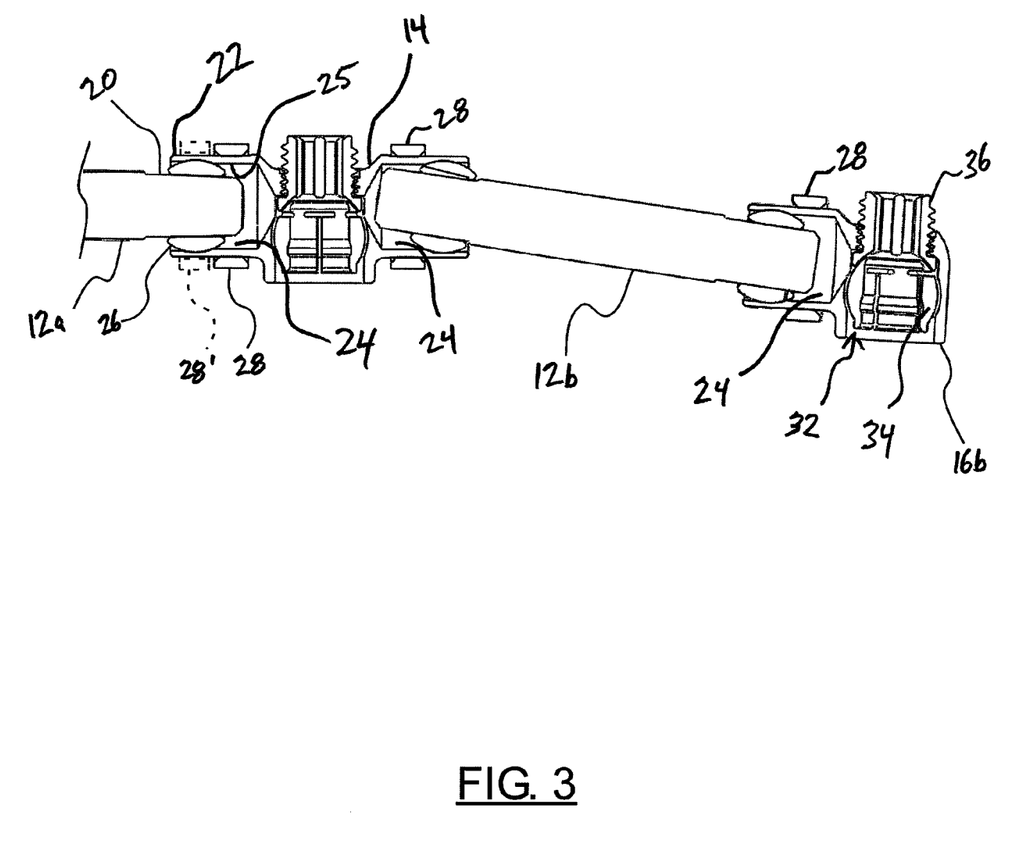
FIG. 3 is a sectioned view of the linking rod assembly and coupler of FIG. 2, shown attached to a second linking rod and second, end coupler.

Turning to FIGS. 2 and 3, specific aspects of one embodiment of the invention are shown in greater detail. In this embodiment, connector rod body 12a includes at least one male member 20 (two are shown, one on each end of the connector rod). "T" coupler body 14 can include one or more female members 22 that can include an internal bore (best seen at 24 in FIG. 3). The internal bore of the female member and the male member can be cooperatively sized and shaped such that the male member fits easily within the female member.

Coupling or attaching of the male member 20 to the female member 22 can be accomplished in a number of manners. In one embodiment of the invention, the male member includes a raised portion 26 that can be formed on or attached to the male member. The internal bore 24 of the female member can include an area of decreased diameter associated therewith. The area of decreased diameter (25 in FIG. 3), while not always event to the human eye, is created in the embodiment shown in FIG. 3 immediately beneath a cinch band 28. In this aspect, the cinch band fits about an outer portion of the female member and applies a compressive force to the female member. This compressive force is translated though the barrel or cylinder of the female member such that the inner bore is slightly decreased in diameter beneath the cinch band.

To couple the connector rod body 12a to the "T" coupler body 14, the raised portion 26 of the male member 20 and the area of decreased diameter 25 within the bore of the female member 22 are positioned adjacent one another and an interference fit is created between the two bodies. This condition is shown by the displaced cinch band 28' in FIG. 3. Thus, in this embodiment, the cinch band 28 is moveable or slidable along the outer portion of the female member 22. In one example, the cinch band is fitted about the outer portion of the female member such that a force of about 800 pounds is required to move the cinch band along the outer portion. Since the position of the cinch band is adjustable, the location at which the male member and the female member are coupled to one another can be adjusted. That is, the raised portion of the male member can be positioned in a variety of locations within the bore of the female member, after which the cinch band can be positioned over the raised portion to fix or attach or couple the bodies one to another.

While a sliding cinch band 28 is shown in the figures, it is to be understood that the area of decreased diameter 25 within the bore 24 of the female member 22 can be accomplished in a number of manners. In one aspect of the invention, the area of decreased diameter can be a permanent feature formed within the bore. In another aspect, the cinch band can be very loosely fitted about the outer portion of the female member (such that almost no force is required to move it along the length of the outer portion), and it can be clamped into position about the outer portion where desired. In yet another aspect, the cinch band can be formed from a shape memory alloy that can be activated by a change in temperature or by stress. A variety of other methods can be used to accomplish this result, so long as the resultant force applied by the cinch band is sufficient to create the area of decreased diameter within the bore of the female member.

In the aspect of the invention shown in FIGS. 2 and 3, the raised portion 26 of the male member 20 is moveably attached to the male member so as to be selectively positionable along at least a portion of a length of the male member. This provides further adjustability to the system, allowing a doctor to "fine tune" the position where the two bodies 12a and 14 (in this example) are coupled to one another, to allow precise adjustments to the construct. In the embodiment shown, the raised portion comprises a band that is snugly fitted about the male member such that the band generally remains in position during the procedure, but can be relatively easily moved by a doctor: even allowing adjustments by finger force prior to inserting the male member within the female member.

The raised portion 26 can include a generally spherical outer contour that allows the coupling rod body 12a to be rotated relative to the "T" coupler 14 (or other body) to provide easy adjustments in angle between bodies. As shown, for example, in FIG. 3, the leftmost connector rod 12a is substantially in-line with the leftmost inner bore of "T" coupler 14, while the rightmost connector rod 12b can be positioned at a significant angle relative to the axis of the rightmost inner bore of the "T" coupler. In each case, the present system allows the connector rods 12a, 12b to be easily and securely coupled, via an interference fit, to the "T" coupler. Thus, the raised portion 26 allows for translational adjustments (as it can be slid along the male portion) and rotational adjustments (as it can be rotated within the bore of the female member). Also, the cinch band 28 configuration allows for further translational adjustment, as it can be cinched about the raised portion in a variety of positions along the length of the female member.

While not so required, the raised portion 26 can include one or more slots (27 in FIG. 2) formed therein that allow the spherical band to more easily compress beneath the area of decreased diameter associated with the female member to provide the interference fit between the first and second bodies. In the embodiment shown, the slots 27 extend from one edge of the band and terminate slightly before reaching the other edge of the band. The slots are also offset from one another (e.g., they alternate beginning on one edge of the band), so that the band is formed from a monolithic piece of material that is substantially symmetrical about an equator of the band.

As shown in FIG. 2, the male member 20 of the connector rod body 12a can include a retaining lip 30 that retains the moveable raised portion (or band) 26 on the male member shaft, to prevent the band from falling off of the shaft during initial assembly of the construct. Due to the flexibility provided to the band by the slots 27, the band can expand slightly in the configuration shown in FIG. 2 to fit over the retaining lip while the male member is outside of the bore 24 of the female member. However, once positioned inside the bore of the female member, the band can slide but cannot expand enough to pass beyond the retaining lip 30. Thus, there is little to no risk that the band can slide off the male member during installation of the construct.

In the system shown, the various bodies 12a, 16a, 14, etc., can be coupled to one another by an interference fit that effectively locks the components in position relative to one another once implanted into a patient. However, due to the unique design elements of the raised portion (or band) 26 and the cinch band 28, the interference fit can be created elastically. In this manner, all of the components utilized can be disengaged (or uncoupled) from one another, and will return to their original condition (e.g., their original shape, dimensions, etc.). Thus, the present system can be disassembled and used again if, for example, the surgeon wishes to readjust the various components after installation, or if later surgery requires dismantling, adjustment or additions to the system.

One or more of the bodies 12a, 14, 16a, 16b, 16c, etc., can include a receptacle (32 in FIG. 3, for example) formed therein that can be operable to receive a head portion of a surgical screw to allow implantation of the assembly within a body of a patient. In some embodiments of the invention, a ball socket 34 can be positioned within the receptacle 32 to facilitate a secure connection to the head of the surgical screw. FIG. 3 illustrates one manner in which the ball socket 34 can be coupled to the screw head. In this example, a threaded set screw 36 can be positioned above the ball socket. Once the head of the surgical screw (not shown in FIG. 3) is inserted into the ball socket, the set screw can be turned downward to compress and lock the ball socket over the head of the surgical screw. See, for example, FIG. 4B, where the center surgical screw 18b is locked into position within "T" coupler 14, while the outer two surgical screws have not yet been locked into position (the set screws on these couplers have not yet been threaded down to force the ball socket into position around the surgical screws).

While set screw 36, shown in most of the embodiments, remains in place over the ball socket 34, it is to be understood that a removable set screw could also be utilized. This is due to the design of the ball socket, which becomes locked in place over the head of the surgical screws and remains in place unless it becomes necessary to remove the body from the surgical screw. In addition, a tool or implement could be used to lock the ball socket in place over the head of the surgical screw, and no set screw would be required.

The present invention advantageously provides a surgeon with a great deal of latitude when deciding the order in which the various components of the system will be coupled one to another. Thus, the sequence of locking can be varied depending on what the surgeon is attempting to do to manipulate bone position. Specifically, the surgeon may choose a unique sequence of locking rods-to-couplers or couplers-to-bone screws for each of several surgical maneuvers (e.g. in spinal surgery he might employ unique sequences to reduce a spondylolisthesis, correct scoliosis, change lordosis, manipulate disc space height, etc.). The novel segmentation of rods and unique mechanism for locking simplify surgical correction of bones.

Figure 4A:
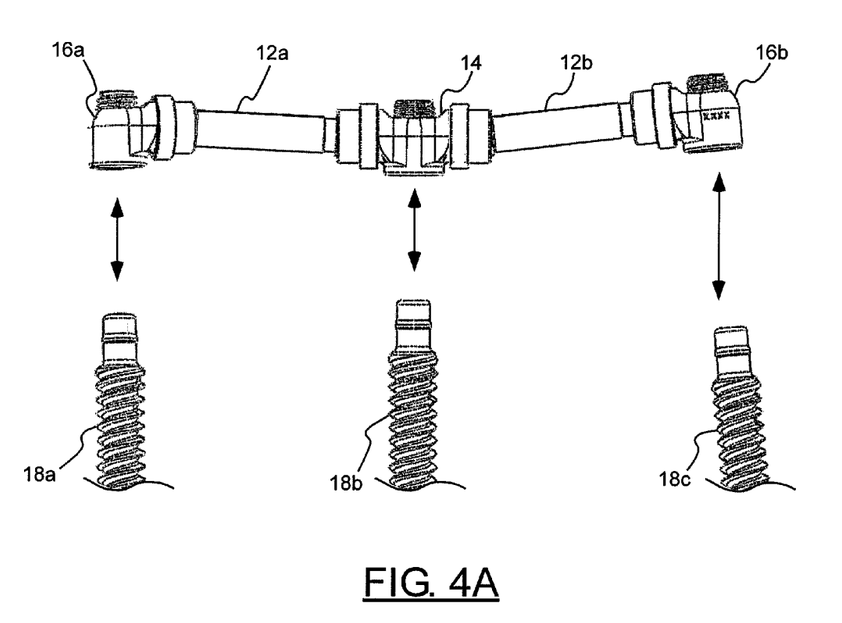
FIG. 4A is a partially exploded view of the system of FIG. 1.

FIGS. 4A through 4D illustrate one exemplary manner of attaching a series of connector rods (12a, 12b) coupled to a series of bodies (16a, 14 and 16b) which will be attached to a series of surgical screws (18a, 18b and 18c). In FIG. 4A, the sequence begins by inserting male portions of connector rods 12a, 12b into female bores of connectors (or bodies) 16a, 14 and 16b. Each body can then be lowered into place over its respective surgical screw. Note that, in this example, none of the components are fixed relative to one another immediately after the bodies are lowered onto the surgical screws.

Figure 4B:
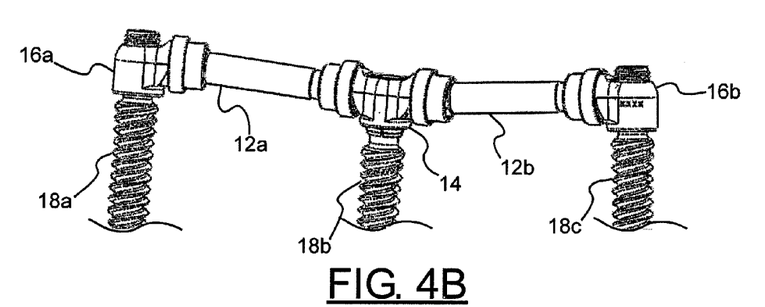
FIG. 4B illustrates the system of FIG. 4A, with the couplers moved into position atop the surgical screws, and with the center coupler fixed to the center surgical screw.
Figure 4C:
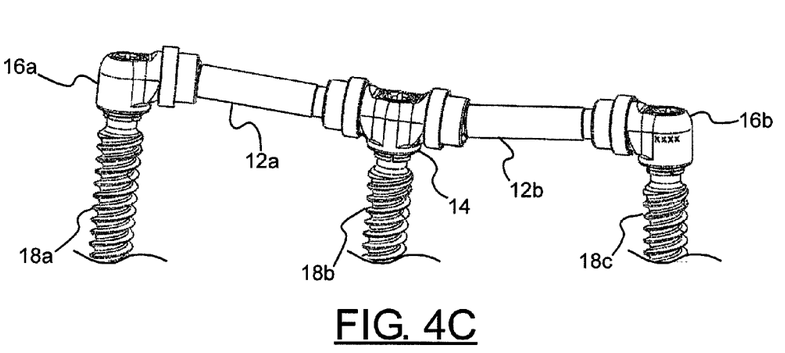
FIG. 4C illustrates the system of FIG. 4A with each of the couplers fixed to their respective surgical screws.
Figure 4D:
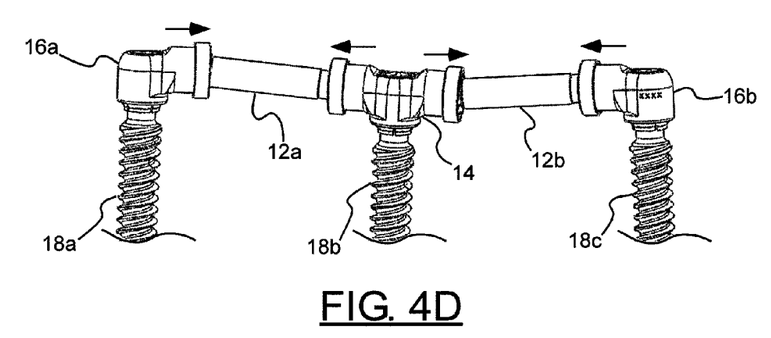
FIG. 4D illustrates the system of FIG. 4A with each of the couplers fixed to their respective counterparts.

In FIG. 4B, it can be seen that "T" coupler 14 has been attached or fixed to surgical screw 18b, but none of the remaining components have been fixed. In FIG. 4C, it can be seen that all of the bodies (16a, 14 and 16b) have been fixed or coupled to their respective surgical screws (18a, 18b and 18c, respectively). However, none of the bodies have yet been fixed to the connector rods 12a, 12b. Finally, in FIG. 4D, it can be seen that each of the cinch bands 26 has been moved into its "locked" position (as shown by directional indicators 29) such that all components of the construct are now rigidly fixed or coupled one to another.

One of ordinary skill in the art, having possession of this disclosure, could readily appreciate that a different order or fixing the various components could be utilized if the surgeon wished to accomplish a different result.

In addition to the apparatus discussed above, the present invention also provides various methods of coupling components of surgical constructs, and implanting surgical constructs. In one embodiment, a method of coupling portions of a surgical construct to one another is provided, including: obtaining a first body and a second body, one of the first body and the second body including a male member and an other of the first body and the second body including a female member, the male member being sized and shaped to be received within the female member and the female member having an internal bore sized and shaped to receive the male member therein; positioning a raised portion formed on or attached to the male member within the internal bore of the female member; and creating an area of decreased diameter within the internal bore of the female member about or around the raised portion of the male member to thereby couple the first body and the second body to one another by an interference fit.

In another aspect, a method of implanting a coupling assembly within a patient is provided, including: attaching one of a first body and a second body to a first surgical screw, one of the first body and the second body including a male member and an other of the first body and the second body including a female member, the male member being sized and shaped to be received within the female member and the female member having an internal bore sized and shaped to receive the male member therein; positioning a raised portion formed on or attached to the male member within the internal bore of the female member; and creating an area of decreased diameter within the internal bore of the female member about or around the raised portion of the male member to thereby couple the first body and the second body to one another by an interference fit.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

We claim:

1. A coupling assembly for use in surgical constructs, comprising:
   a first body and a second body;
   one of the first body and the second body including a male member and an other of the first body and the second body including a female member, the male member being sized and shaped to be received within the female member and the female member having an internal bore sized and shaped to receive the male member therein;
   a raised portion formed on or attached to the male member;
   the female member being cylindrical in shape and including an outer portion having a length coincident with a length of the internal bore of the female member;
   an area of decreased diameter associated with the internal bore of the female member, the area of decreased diameter being adjustably positionable along the length of the internal bore of the female member;
   the first and second bodies being coupleable to one another by an interference fit when the raised portion of the male member is positioned within the area of decreased diameter associated with the internal bore of the female member.

2. The assembly of claim 1, wherein the raised portion is moveably attached to the male member so as to be selectively positionable along at least a portion of a length of the male member.

3. The assembly of claim 2, wherein the raised portion comprises a spherical band moveably attached to the male member.

4. The assembly of claim 3, wherein the spherical band includes one or more slots formed therein that allow the spherical band to more easily compress beneath the area of decreased diameter associated with the female member to provide the interference fit between the first and second bodies.

5. The assembly of claim 1, wherein the area of decreased diameter associated with the internal bore of the female member is created by a cinch band positioned on the outer portion of the female member, the cinch band operable to compress the female member to create the area of decreased diameter within the internal bore of the female member.

6. The assembly of claim 5, wherein the cinch band applies substantially the same compressive force to the outer portion of the female member as it is slid along the length of the outer portion of the female member.

7. The assembly of claim 5, wherein the cinch band is slidably moveable along the length of the outer portion of the female member so as to be selectively positionable over the raised portion of the male member to create the interference fit between the first and second bodies.

8. The assembly of claim 1, wherein the interference fit created between the first and second bodies is created elastically, such that the first and second bodies return to an original configuration when uncoupled.

9. The assembly of claim 1, wherein at least one of the first and second bodies includes a receptacle operable to receive a head portion of a surgical screw to allow implantation of the assembly within a body of a patient.

10. A coupling assembly for use in surgical constructs, comprising:
    a first body and a second body;
    one of the first body and the second body including a male member and an other of the first body and the second body including a female member, the male member being sized and shaped to be received within the female member and the female member having an internal bore sized and shaped to receive the male member therein;
    the female member being cylindrical in shape and including an outer portion having a length coincident with a length of the internal bore of the female member;
    a raised portion formed on or attached to the male member;
    a cinch band applied to the outer portion of the female member, the cinch band being slidable along the length of the outer portion of the female member, the cinch band applying a compressive force to the female member to create an area of decreased diameter within the internal bore of the female member;
    the first and second bodies being coupleable to one another by an interference fit when the raised portion of the male member is positioned within the area of decreased diameter in the internal bore of the female member.

11. The assembly of claim 10, wherein the raised portion is moveably attached to the male member so as to be selectively positionable along a length of the male member.

12. The assembly of claim 11, wherein the raised portion comprises a spherical band moveably attached to the male member.

13. The assembly of claim 12, wherein the spherical band includes one or more slots formed therein that allow the spherical band to more easily compress beneath the area of decreased diameter associated with the female member to provide the interference fit between the first and second bodies.

14. The assembly of claim 10, wherein the cinch band is slidably moveable along the length of the outer portion of the female member so as to be selectively positionable over the raised portion of the male member to create the interference fit between the first and second bodies.

* * * * *